United States Patent
Stock et al.

(10) Patent No.: US 10,196,370 B2
(45) Date of Patent: Feb. 5, 2019

(54) METHOD FOR THE EPOXIDATION OF AN OLEFIN WITH HYDROGEN PEROXIDE

(71) Applicant: Evonik Degussa GmbH, Essen (DE)

(72) Inventors: Jürgen Stock, Frankfurt (DE); Joao André, BA Maastricht (NL); Sebastian Imm, Bad Vilbel (DE); Matthias Pascaly, Frankfurt (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/550,872

(22) PCT Filed: Feb. 3, 2016

(86) PCT No.: PCT/EP2016/052273
§ 371 (c)(1),
(2) Date: Aug. 14, 2017

(87) PCT Pub. No.: WO2016/131652
PCT Pub. Date: Aug. 25, 2016

(65) Prior Publication Data
US 2018/0030012 A1 Feb. 1, 2018

(30) Foreign Application Priority Data
Feb. 17, 2015 (EP) ................... 15155413

(51) Int. Cl.
*C07D 301/12* (2006.01)
*C07D 303/02* (2006.01)
*B01D 61/02* (2006.01)
*B01J 23/34* (2006.01)
*C07C 11/04* (2006.01)
*C07C 11/06* (2006.01)
*C07C 21/067* (2006.01)

(52) U.S. Cl.
CPC ......... *C07D 301/12* (2013.01); *B01D 61/027* (2013.01); *C07D 303/02* (2013.01); *B01J 23/34* (2013.01); *C07C 11/04* (2013.01); *C07C 11/06* (2013.01); *C07C 21/067* (2013.01)

(58) Field of Classification Search
CPC .. C07D 301/12; C07D 303/02; B01D 61/027; B01J 23/34; C07C 21/067; C07C 11/04; C07C 11/06
See application file for complete search history.

(56) References Cited

U.S. PATENT DOCUMENTS

| | | |
|---|---|---|
| 5,242,602 A | 9/1993 | Richardson et al. |
| 5,274,140 A | 12/1993 | Venturello et al. |
| 5,329,024 A | 7/1994 | Jureller et al. |
| 6,288,248 B1 | 9/2001 | Strebelle et al. |
| 6,500,311 B1 | 12/2002 | Sawyer |
| 6,673,950 B1 | 1/2004 | Teles et al. |
| 6,774,992 B1 | 8/2004 | Garver et al. |
| 8,802,873 B2 | 8/2014 | Postma et al. |
| 9,024,048 B2 | 5/2015 | Kapellen et al. |
| 9,371,300 B2 | 6/2016 | Kapellen et al. |
| 10,087,158 B2 | 10/2018 | Stock et al. |
| 2002/0004606 A1 | 1/2002 | Thiele |
| 2003/0171604 A1 | 9/2003 | Mizuno et al. |
| 2005/0171100 A1 | 8/2005 | Pavey |
| 2007/0032671 A1 | 2/2007 | Shinohara et al. |
| 2011/0137054 A1 | 6/2011 | Postma et al. |
| 2011/0137055 A1 | 6/2011 | Postma et al. |
| 2012/0289722 A1 | 11/2012 | Muppa et al. |
| 2014/0113801 A1 | 4/2014 | Kapellen et al. |
| 2014/0296545 A1 | 10/2014 | Postma et al. |

FOREIGN PATENT DOCUMENTS

| | | |
|---|---|---|
| EP | 0 559 305 | 9/1993 |
| EP | 2 537 836 | 12/2012 |
| WO | WO 2004/028962 | 4/2004 |
| WO | WO 2004/043941 | 5/2004 |
| WO | WO 2010/012360 | 2/2010 |
| WO | WO 2010/012361 | 2/2010 |
| WO | WO 2010/145901 | 12/2010 |
| WO | WO 2011/062608 | 5/2011 |
| WO | WO 2011/063937 | 6/2011 |
| WO | WO 2011/107188 | 9/2011 |
| WO | WO 2012/175182 | 12/2012 |
| WO | WO-2013/113578 | 8/2013 |
| WO | WO 2014/056603 | 4/2014 |
| WO | WO 2016/131649 | 8/2016 |
| WO | WO 2016/131650 | 8/2016 |
| WO | WO 2016/131858 | 8/2016 |

OTHER PUBLICATIONS

Letki, A., "Separation, Centrifugal Separation. vol. 5" Kirk-Othmer Encyclopedia of Chemical Technology (1997) p. 505-551.*
International Search Report for corresponding international application PCT/EP2016/052273 filed Feb. 3, 2016.
Written Opinion of the International Searching Authority for corresponding international application PCT/ EP2016/052273 filed Feb. 3, 2016.
International Preliminary Report on Patentability for corresponding international application PCT/2016/052273 filed Feb. 3, 2016.
PCT Direct Letter for PCT/EP2016/052273 filed by Applicant during International Stage and dated Dec. 22, 2015.
(Continued)

*Primary Examiner* — John M Mauro
(74) *Attorney, Agent, or Firm* — Law Office of: Michael A. Sanzo, LLC

(57) ABSTRACT

In the method for the epoxidation of an olefin, the olefin is continuously reacted with hydrogen peroxide in a mixed reactor in the presence of a water soluble epoxidation catalyst, comprising a manganese complex, the reaction is carried out in a reaction mixture comprising an aqueous liquid phase and an organic liquid phase with mixing of the liquid phases, reaction mixture is continuously withdrawn from the mixed reactor and separated into a separated aqueous phase and a separated organic phase, and part of the separated aqueous phase is continuously recycled into the mixed reactor, with the combined hold-up time of aqueous phase in withdrawing, separating phases and recycling aqueous phase being kept at less than 15 minutes.

16 Claims, 1 Drawing Sheet

(56) References Cited

OTHER PUBLICATIONS

European Search Report and Opinion for EP 15 155 413.6 completed Apr. 21, 2015 for corresponding international application PCT/ EP2016/052273.
International Search Report for related international application PCT/EP2016/052216 filed Feb. 3, 2016.
Written Opinion of the International Searching Authority for related international application PCT/EP2016/052216 filed Feb. 3, 2016.
International Preliminary Report on Patentability for related international application PCT/EP2016/052216 filed Feb. 3, 2016.
PCT Direct Letter for PCT/EP2016/052216 filed by Applicant during International Stage and dated Nov. 3, 2015.
International Search Report for related international application PCT/EP2016/052222 filed Feb. 3, 2016.
Written Opinion of the International Searching Authority for related international application PCT/EP2016/052222 filed Feb. 3, 2016.
International Preliminary Report on Patentability for related international application PCT/EP2016/052222 filed Feb. 3, 2016.
PCT Direct Letter for PCT/EP2016/052222 filed by Applicant during International Stage and dated Jan. 18, 2016.
European Search Report and Opinion for EP 15155418.4 completed Apr. 23, 2015 for international application PCT/EP2016/052222.
International Search Report for related international application PCT/EP2016/053340 filed Feb. 17, 2016.
Written Opinion of the International Searching Authority for related international application PCT/EP2016/053340 filed Feb. 17, 2016.
International Preliminary Report on Patentability for related international application PCT/EP2016/053340 filed Feb. 17, 2016.
PCT Direct Letter for PCT/EP2016/053340 filed by Applicant during International Stage and dated Feb. 9, 2016.
De Vos, et al., "Epoxidation of Terminal of Electron-deficient Olefins with $H_2O_2$, catalysed by Mn-trimethyltiazacyclonane Complexes in the Presence of an Oxalate Buffer," *Tetrahedron Letters* 39(20):3221-3224 (May 1998).

U.S. Appl. No. 15/550,856, filed Aug. 14, 2017, Stock.
U.S. Appl. No. 15/550,836, filed Aug. 14, 2017, Stock.
U.S. Appl. No. 15/550,814, filed Aug. 14, 2017, Breitenbach.
Berkessel, "Biomimetic Oxidation of Organic Substrates with Hydrogen Peroxide," *TCI Mail* 109:3-13 (2001).
Yang, et al., "Catalase and Epoxidation Activity of Manganese Salen Complexes Bearing Two Xanthene Scaffolds," *Journal of the American Chemical Society* 129(26):8192-8198 (published online Jun. 2007).
English language machine translation of WO 2013/113578 published on Aug. 8, 2013.
Office Action for copending U.S. Appl. No. 15/550,836 dated Dec. 27, 2017.
Office Action for copending U.S. Appl. No. 15/550,856 dated Dec. 11, 2017.
Response to Office Action dated Dec. 11, 2017 for copending U.S. Appl. No. 15/550,856, filed Mar. 12, 2018.
Notice of Allowance for copending U.S. Appl. No. 15/550,856 dated May 31, 2018.
Office Action for copending U.S. Appl. No. 15/550,814 dated Jun. 18, 2018.
Berkessel, et al., "Biomimetic Oxidation of Organic Substrates with Hydrogen Peroxide," *Institit fur Organische Chemie der Universitat zu Koln, Griemstr4*:1-11 (2001).
Blake, et al., "8.48 pH Measurement," Process Measurement and Analysis ed. B.G. Liptak CRC Press p. 1565-1584.
Liptak, Control Global https://www.controlglobal.com/articles/2008/183/:p. 1-2.
Venturello, et al., "A new, effective catalytic system for epoxidation of olefins by hydrogen peroxide under phase-transfer conditions," *The Journal of Organic Chemistry* 48.21:3831-3833 (1983).
Response to Office Action filed Sep. 17, 2018 for copending U.S. Appl. No. 15/550,814.
Notice of Allowance dated Oct. 26, 2018 for copending U.S. Appl. No. 15/550,814.

* cited by examiner

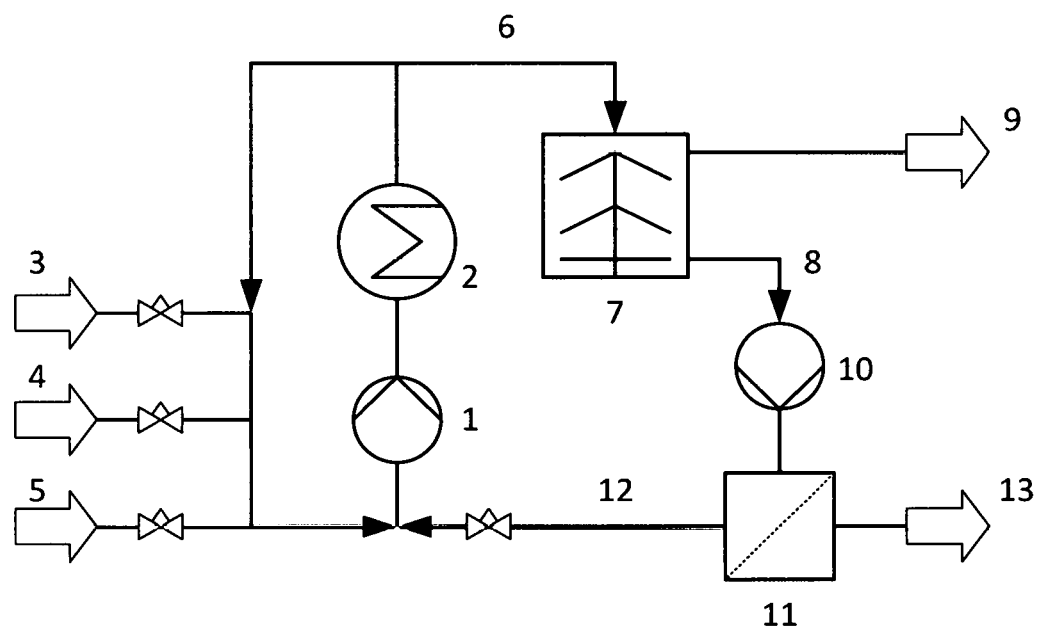

METHOD FOR THE EPOXIDATION OF AN OLEFIN WITH HYDROGEN PEROXIDE

CROSS REFERENCE TO RELATED APPLICATIONS

The present application is US national stage of international application PCT/EP2016/052273, which had an international filing date of Feb. 3, 2016, and which was published in English under PCT Article 21(2) on Aug. 25, 2016. The application claims priority to European application 15155413.6, filed on Feb. 17, 2015.

FIELD OF THE INVENTION

The invention relates to a method for the epoxidation of an olefin with hydrogen peroxide in the presence of a water soluble epoxidation catalyst comprising a manganese complex where the reaction is carried out in a reaction mixture comprising an aqueous liquid phase and an organic liquid phase and the catalyst is recycled.

BACKGROUND OF THE INVENTION

Methods for the epoxidation of an olefin with hydrogen peroxide using a water soluble manganese complex as epoxidation catalyst are known from D. E. De Vos et al., Tetrahedron Letters 39 (1998) 3221-3224 and from U.S. Pat. No. 5,329,024.

WO 2010/012360 discloses epoxidation of allyl chloride in an aqueous reaction medium with a water soluble manganese complex as epoxidation catalyst. The reaction product epichlorohydrin forms an organic phase and a settler may be used to optimize gravitational separation of the epichlorohydrin. A membrane unit may be used to recycle the aqueous reaction medium with reduced loss of catalyst.

WO 2011/107188 discloses use of a loop reactor for epoxidation with this catalyst in a multiphasic reaction mixture comprising an organic phase and an aqueous phase. Reaction mixture withdrawn from the loop reactor is separated into an aqueous phase and an organic phase in a settler and aqueous phase is recycled to the loop reactor.

WO 2012/175182 teaches that the manganese complex cannot be successfully recycled with the separated aqueous phase because it deactivates during phase separation when the aqueous phase is not intensively mixed with the organic phase. The document further teaches that such deactivation can be avoided by lowering the pH of the aqueous phase before carrying out phase separation. However, the catalyst has low catalytic activity for epoxidation at the low pH needed for stabilizing the catalyst and the pH has to be raised again for efficiently reusing the catalyst in the epoxidation reaction. The catalyst recycling proposed in WO 2012/175182 therefore leads to salt formation from the acid and the base which have to be added for lowering and increasing the pH of the aqueous phase.

SUMMARY OF THE INVENTION

It has now been found that manganese complex can be recycled with the separated aqueous phase without the need for adding an acid when phase separation and recycling of separated aqueous phase into the reactor are performed continuously within less than 15 minutes, preferably within less than 2 minutes.

It has further been found that sufficiently fast continuous phase separation can be achieved by centrifugal force, preferably by a centrifuge.

It has also been found that more catalyst can be recycled by nanofiltration of the separated aqueous phase with enrichment of the manganese complex in the retentate.

Subject of the invention is therefore a method for the epoxidation of an olefin, comprising
a) continuously reacting the olefin with hydrogen peroxide in a mixed reactor in the presence of a water soluble epoxidation catalyst, comprising a manganese complex, the reaction being carried out in a reaction mixture comprising an aqueous liquid phase and an organic liquid phase with mixing of the liquid phases,
b) continuously withdrawing reaction mixture from the mixed reactor and separating the withdrawn reaction mixture into a separated aqueous phase and a separated organic phase, and
c) continuously recycling part of the separated aqueous phase into the mixed reactor,
wherein the combined hold-up time of aqueous phase in steps b) and c), defined as the ratio of the total volume occupied by aqueous phase in steps b) and c) to the volumetric flow rate of recycled separated aqueous phase, is less than 15 minutes.

BRIEF DESCRIPTION OF DRAWINGS

The FIGURE included herewith shows a preferred embodiment of the method of the invention using a loop reactor as mixed reactor, phase separation in a conical plate centrifuge and recycling of separated aqueous phase with nanofiltration

DETAILED DESCRIPTION OF THE INVENTION

In the method of the invention an olefin is reacted with hydrogen peroxide in the presence of a water soluble epoxidation catalyst in a reaction mixture comprising an aqueous liquid phase and an organic liquid phase.

The olefin may contain one or several carbon-carbon double bonds. In olefins containing two or more double bonds, the double bonds may be isolated or conjugated, isolated double bonds being preferred. The olefin may be linear, branched or cyclic and may carry substituents, in particular one or more substituents selected from aryl groups, halogens, free and esterified hydroxyl groups, alkoxy groups and carboxyl groups. The substituents may be in vinylic or allylic position or bonded to another position of the olefin, with substituents in allylic position being preferred.

The olefin preferably has a solubility in water of from 0.01 g/L to 100 g/L at 20° C., more preferably of from 0.01 g/L to 10 g/L at 20° C., in order to achieve both a high rate of reaction in epoxidation and formation of an organic liquid phase without addition of solvent.

In a preferred embodiment, the olefin is allyl chloride and the method of the invention provides epichlorohydrin as the reaction product. In another preferred embodiment, the olefin is propene and the method of the invention provides propene oxide as the reaction product.

Hydrogen peroxide can be used as an aqueous solution, preferably containing from 20 to 75% by weight hydrogen peroxide and most preferably from 40 to 70% by weight. Preferably, an aqueous hydrogen peroxide solution prepared by an anthraquinone process is used. A crude hydrogen peroxide solution as obtained in the extraction step of the anthraquinone process may be used in the method of the invention.

The water soluble epoxidation catalyst comprises a manganese complex. The manganese complex preferably comprises at least one polydentate ligand which preferably coordinates through nitrogen atoms, most preferably through tertiary amino groups. The manganese complex may be a mononuclear complex of formula $[LMnX_m]Y_n$, a dinuclear complex of formula $[LMn(\mu-X)_mMnL]Y_n$ or a polynuclear complex of formula $[L_pMn_p(\mu-X)_m]Y_n$, where L is a polydentate ligand, X is a coordinating species, $\mu$-X is a bridging coordinating species, Y is a non-coordinating counter ion, m is 1, 2 or 3, n is an integer providing for the charge neutrality of the complex, and p is from 3 to 5. X and $\mu$-X are preferably selected from the group consisting of $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $ROSO_3^-$, $OH^-$, $O^{2-}$, $O_2^{2-}$, $HOO^-$, $H_2O$, $SH^-$, $CN^-$, $OCN^-$, $C_2O_4^{2-}$ and $SO_4^{2-}$, where R is alkyl, cycloalkyl, aryl or aralkyl with no more than 20 carbon atoms. Y is preferably selected from the group consisting of $RO^-$, $Cl^-$, $Br^-$, $I^-$, $F^-$, $RCOO^-$, $SO_4^{2-}$, $PF_6^-$, p-tolylsulfonate and trifluoromethylsulfonate, where R is alkyl, cycloalkyl, aryl or aralkyl with no more than 20 carbon atoms. Manganese may be in the oxidation state +2, +3, +4, or +7, the oxidation states +3 and +4 being preferred.

Preferred polydentate ligands are acyclic polyamines containing at least 7 atoms in the backbone or cyclic polyamines containing at least 9 atoms in the ring, each having the nitrogen atoms separated by at least two carbon atoms. Most preferred are ligands having a 1,4,7-triazacyclononane (Tacn) ring system, which may be substituted with one or more alkyl, cycloalkyl, aryl or aralkyl groups each containing up to 20 carbon atoms. Preferred substituents are methyl groups. Suitable ligands with a Tacn ring system are N',N',N'''-trimethyl-1,4,7-triazacyclononane (TmTacn) and 2-methyl-1,4,7-trimethyl-1,4,7-triazacyclononane, with TmTacn being preferred. Another suitable ligand is 1,5,9-trimethyl-1,5,9-triazacyclododecane.

Most preferred are the dinuclear manganese complexes $[(TmTacn)Mn^{IV}(\mu-O)_3Mn^{IV}(TmTacn)](PF_6)_2$ and $[(TmTacn)Mn^{IV}(\mu-O)_3Mn^{IV}(TmTacn)](CH_3COO)_2$.

The manganese complex may be formed in the reaction mixture by reaction of the polydentate ligand with a manganese salt, preferably manganese sulfate, manganese acetate, manganese nitrate, manganese chloride or manganese bromide with $Mn^{2+}$ or $Mn^{3+}$. Preferably, the manganese complex is prepared separately and added to the reaction mixture.

The water soluble epoxidation catalyst preferably comprises oxalic acid, an oxalate or a mixture of both as a co-catalyst in addition to the manganese complex. The co-catalyst is preferably used in a molar excess to the manganese complex, preferably with a molar ratio of co-catalyst to manganese complex in the range of from 10:1 to 10 000:1.

The reaction is carried out in a reaction mixture comprising an aqueous liquid phase and an organic liquid phase with mixing of the liquid phases. Preferably, the ratio of the volume of the aqueous phase to the volume of the organic phase is maintained in the range of from 10:1 to 1:10, more preferably from 2:1 to 1:4. Mixing of the liquid phases can be performed by turbulent flow of the reaction mixture, by passing reaction mixture through fixed mixing elements, such as static mixers, structured packings or random packings, or by a moving mixing element, such as a stirrer or a rotating pump.

The aqueous phase preferably comprises less than 30% by weight, more preferably less than 5% by weight of a solvent. The organic phase may contain a water insoluble solvent, but preferably contains less than 30% by weight, more preferably less than 5% by weight of a solvent. In both instances the term solvent refers to compounds added in addition to olefin, epoxidation catalyst, co-catalyst and impurities introduced with these components, and does not encompass products formed from the olefin.

The epoxidation reaction is preferably carried out at a temperature of from 0° C. to 70° C., more preferably from 5° C. to 40° C. and most preferably from 10° C. to 30° C. When the boiling point of the olefin at 1 bar is close to or higher than the reaction temperature, the epoxidation is carried out at elevated pressure to maintain the olefin in the liquid phase. When the olefin is propene, the epoxidation reaction is preferably carried out at a pressure of from 0.8 to 2.0 MPa. When the olefin is allyl chloride, the epoxidation reaction is preferably carried out at a pressure of from 0.12 to 1.0 MPa.

The reaction is carried out continuously in a mixed reactor. The mixed reactor may be a continuous stirred tank reactor (CSTR), a continuous flow reactor comprising mixing elements or preferably a loop reactor. The term loop reactor here refers to a reactor in which reaction mixture is circulated driven by a pump. Pumping of the reaction mixture provides mixing of the liquid phases. The loop reactor may comprise vessels for increasing the volume in the loop and providing the residence time necessary for achieving the desired hydrogen peroxide conversion. Preferably, further mixing of the reaction mixture is provided in such vessels, for example by static mixers, structured packings or random packings arranged in a tube of enlarged diameter or by a stirred vessel arranged in the reactor loop. Preferably, a heat exchanger is arranged in the loop for cooling the reaction mixture in order to remove the heat of reaction, the reaction mixture preferably being passed through the heat exchanger in every cycle of the loop. The heat exchanger is preferably a tube bundle heat exchanger with the reaction mixture being passed through the tubes or a plate heat exchanger. The diameter of the tubes or the distance between plates is preferably chosen sufficiently narrow for providing turbulent flow and mixing of the two liquid phases.

When a loop reactor is used as mixed reactor, the average residence time in the loop reactor, calculated as the ratio of the volume of the loop reactor divided by the sum of all fluid flows entering the loop reactor, is preferably selected to provide a hydrogen peroxide conversion of more than 85%, more preferably of from 95% to 99.5%. For this purpose, the average residence time is preferably from 20 to 240 min.

In the mixed reactor the pH of the aqueous phase is preferably maintained in the range of from 2 to 6 and more preferably 2.5 to 5. Preferably, a buffer is added to stabilize the pH in this range. The buffer may be an inorganic buffer, such as a phosphate buffer, or preferably an organic buffer, such as a carboxylic acid/carboxylate buffer. Most preferably, an oxalic acid/oxalate buffer is used, which acts both as buffer and as co-catalyst. The buffer may be prepared previous to feeding it to the mixed reactor or may be preferably generated within the mixed reactor by separately feeding an acid and a base to the mixed reactor. More preferably, aqueous solutions of oxalic acid and sodium hydroxide are fed separately to the mixed reactor and most preferably the solution of oxalic acid is fed at an essentially constant rate and the feeding of the sodium hydroxide solution is adjusted to maintain the pH in the desired range.

The olefin is preferably used in molar excess to hydrogen peroxide in step a) in order to achieve high conversion of hydrogen peroxide and the molar ratio of olefin fed to the mixed reactor to hydrogen peroxide fed to the mixed reactor is preferably from 1.2:1 to 12:1, more preferably from 2:1 to 8:1. The amount of catalyst fed to the mixed reactor is preferably chosen to provide a molar ratio of hydrogen peroxide fed to the mixed reactor to manganese fed to the mixed reactor of from 100:1 to 10 000 000:1, more preferably from 1000:1 to 1 000 000:1 and most preferably 10 000:1 to 100 000:1.

In the mixed reactor the concentration of hydrogen peroxide in the aqueous liquid phase is preferably maintained at less than 1.0% by weight during the reaction. Preferably, the concentration of hydrogen peroxide is maintained at from 0.1 to 1.0% by weight, more preferably from 0.2 to 0.7% by weight. The concentration of hydrogen peroxide in the aqueous liquid phase may be adjusted by adjusting the molar ratio of olefin to hydrogen peroxide fed to the mixed reactor, adjusting the feed rate for feeding hydrogen peroxide to the mixed reactor or adjusting the feed rate for feeding epoxidation catalyst to the mixed reactor, with a higher molar ratio of olefin to hydrogen peroxide, a lower feed rate for hydrogen peroxide or a higher feed rate for epoxidation catalyst leading to a lower concentration of hydrogen peroxide in the aqueous liquid phase.

In the method of the invention reaction mixture is continuously withdrawn from the mixed reactor and the withdrawn reaction mixture is separated into a separated aqueous phase and a separated organic phase. The amount of withdrawn reaction mixture preferably corresponds to the total of liquid flows entering the mixed reactor in order to maintain a constant hold-up in the mixed reactor. A part of the separated aqueous phase is continuously recycled into the mixed reactor. The fraction of separated aqueous phase recycled into the mixed reactor is preferably adjusted to maintain a constant phase ratio of aqueous liquid phase to organic liquid phase within the mixed reactor. The fraction of separated aqueous phase that is not recycled may be further processed to recover dissolved non-reacted olefin, epoxide product or reaction by-products or may be discharged.

The combined hold-up time of aqueous phase in the steps of withdrawing reaction mixture from the mixed reactor, separating the withdrawn reaction mixture and recycling a part of the separated aqueous phase into the mixed reactor, defined as the ratio of the total volume occupied by aqueous phase in these steps to the volumetric flow rate of recycled separated aqueous phase, is less than 15 minutes, preferably less than 5 minutes and more preferably less than 2 minutes. As a result, epoxidation catalyst contained in the withdrawn reaction mixture is recycled to the mixed reactor within less than 15 minutes which reduces loss of catalyst activity in the catalyst recycling.

Reaction mixture may be withdrawn from the mixed reactor by an overflow, by a pressure difference between the mixed reactor and the phase separating device or by a pump. The withdrawn reaction mixture may be passed through a heat exchanger for cooling before separating the phases.

Separation of the withdrawn reaction mixture into a separated aqueous phase and a separated organic phase may be carried out with any phase separating device known from the prior art to effect phase separation within considerably less than 15 minutes. Preferably, a phase separating device which applies a centrifugal force to the reaction mixture is used, such as a hydrocyclone or a centrifuge. More preferably, a centrifuge is used as phase separating device in order to provide a low hold-up time. The centrifuge preferably provides an acceleration of at least 20 000 $ms^{-2}$, more preferably of at least 50 000 $ms^{-2}$ and most preferably of at least 70 000 $ms^{-2}$ in order to provide a low hold-up time. The acceleration in the centrifuge preferably does not exceed 250 000 $ms^{-2}$ in order to keep centrifuge construction simple. Most preferably, a conical plate centrifuge is used to achieve a low hold-up time. Phase separation with a centrifuge is particularly preferred when the density difference between the aqueous liquid phase and the organic liquid phase of the reaction mixture is less than 0.1 g/ml, in particular less than 0.05 g/ml, as may be the case for the epoxidation of allyl chloride to epichlorohydrin.

Phase separation is preferably carried out at a temperature that is not more than 5° C. higher than the temperature of the withdrawn reaction mixture and not less than 0° C. The pressure in the phase separation is preferably higher than the vapor pressure of the olefin at the temperature of the phase separation in order to avoid evaporation of olefin.

Recycling part of the separated aqueous phase into the mixed reactor may be performed by simply splitting the separated aqueous phase in the fraction to be recycled and a fraction that is not recycled.

In a preferred embodiment of the method of the invention, the separated aqueous phase is subjected to nanofiltration over a nanofiltration membrane to provide a retentate enriched in manganese complex and all or a part of this retentate is recycled into the mixed reactor. The nanofiltration also provides a permeate depleted in manganese complex which may be further processed to recover dissolved non-reacted olefin, epoxide product or reaction by-products or may be discharged. Since the permeate side of the nanofiltration does not contribute to recycling of aqueous phase, only the volume of the nanofiltration device on the retentate side is considered in calculating the hold-up time of aqueous phase and the hold-up time on the permeate side may be longer than 15 minutes. When the hold-up time on the retentate side of the nanofiltration is considerably less than 15 minutes, the retention of catalyst by nanofiltration increases the amount of active catalyst recycled to the mixed reactor.

The pressure on the permeate side of the nanofiltration is preferably increased relative to the pressure in the mixed reactor using a pump in order to increase trans-membrane flow and is preferably in the range of from 1.5 to 8.5 MPa. The pressure on the permeate side of the nanofiltration is preferably maintained higher than the vapor pressure of the olefin at the temperature of the nanofiltration and is more preferably maintained at a pressure higher than the pressure in the mixed reactor in order to avoid formation of a gas phase in the nanofiltration membrane from evaporating olefin or from oxygen dissolved in the separated aqueous phase. The pressure difference between the permeate side and the retentate side, which drives the nanofiltration, is preferably from 0.5 to 8.0 MPa, more preferably 1.0 to 6.0 MPa and most preferably 2.0 to 4.0 MPa.

Nanofiltration is preferably carried out at a temperature that is not more than 5° C. higher than the temperature of the withdrawn reaction mixture and not less than 0° C.

Nanofiltration is preferably carried out with cross flow over the nanofiltration membrane. Cross flow may be achieved with the continuous flow of the retentate and may be enhanced by a recycle within the nanofiltration unit driven by a pump.

Nanofiltration can be carried out with any nanofiltration membrane which provides retention for the manganese complex in the presence of the olefin and the epoxide.

Suitability of nanofiltration membranes can be tested with routine methods by determining retention of the manganese complex for an aqueous solution of the manganese complex saturated with olefin and epoxide in the absence of hydrogen peroxide. Suitable nanofiltration membranes may comprise an organic polymer or a nanoporous inorganic material as the separation layer. The separation layer is preferably based on an organic polymer selected from aliphatic or aromatic polyamides, polysulfones, polyethersulfones, sulfonated polyethersulfones, cellulose acetate, polypiperazine and polyvinylidenfluoride or a nanoporous layer of silica, alumina, zirconia or titania. Most preferably the separation layer is made from a polyamide or a polyethersulfone. The separation layer may be arranged on a porous support layer which may be from the same material as the separation layer or from a different material. Suitable nanofiltration membranes are commercially available, such as membranes based on polyamides from Trisep, Hydranautics, Toray, Sepro, GE Osmonics, Dow Filmtec and Synder Filtration, membranes based on polysulfone from Koch Membrane Systems, membranes based on polyethersulfone from Microdyn Nadir, membranes based on sulfonated polyethersulfone from Nitto Denko, membranes based on polyacrylonitrile from Koch Membrane Systems, membranes based on cellulose acetate from GE Osmonics, membranes based on polypiperazine from Toray, Koch Membrane Systems and Trisep and membranes based on a nanoporous inorganic material from atech innovations, Pall, TAMI, Pervatech, Inopor and Sterlitech. Examples of suitable commercially available nanofiltration membranes are SelRO™ MPF-34 from Koch Membrane Systems, NADIR® NP030 from Microdyn Nadir and Desal DK from GE Osmonics.

Nanofiltration may be carried out with a flat membrane, a hollow fiber membrane or a spiral wound membrane module, a spiral wound membrane module operated in cross flow being preferred.

The nanofiltration membrane material, the operating conditions for the nanofiltration and the fraction of retentate recycled into the mixed reactor are preferably selected to recycle from 75 to 98% of the total amount of manganese contained in the withdrawn reaction mixture, the remainder being withdrawn with the permeate and optionally a fraction of retentate not recycled to the mixed reactor. Limiting the recycle of manganese avoids accumulation of degradation products of manganese complex in the mixed reactor which can lead to precipitation of manganese oxides in the mixed reactor and as a result to increased hydrogen peroxide decomposition.

The method of the invention is preferably carried out without adding an acid during withdrawal of reaction mixture from the mixed reactor, separation of the withdrawn reaction mixture into a separated aqueous phase and a separated organic phase, and recycling part of the separated aqueous phase into the mixed reactor. More preferably, no acid is added except for adding acid to the mixed reactor. Most preferably, the only addition of acid is an addition of oxalic acid to the mixed reactor. Limiting acid addition in such way reduces the salt load of the aqueous effluent from the epoxidation method.

The FIGURE included herewith shows a preferred embodiment of the method of the invention using a loop reactor as mixed reactor, phase separation in a conical plate centrifuge and recycling of separated aqueous phase with nanofiltration.

The FIGURE included herewith shows a loop reactor comprising a circulation pump (1) and a heat exchanger (2) for cooling the reaction mixture. Catalyst (3) comprising a manganese complex, hydrogen peroxide (4) and olefin (5) are fed to the loop reactor. Buffer and co-catalyst can also be fed to the loop reactor, but are not shown. Reaction mixture (6) is withdrawn in an amount corresponding to the feeds to the loop reactor. The reaction mixture comprises an organic phase, comprising olefin oxide formed by the reaction and non-reacted olefin, and an aqueous phase, comprising hydrogen peroxide, water formed from and introduced with the hydrogen peroxide, epoxidation catalyst and optional additives, such as buffer and co-catalyst. Withdrawn reaction mixture (6) is separated with a conical plate centrifuge (7) into a separated aqueous phase (8) and a separated organic phase (9) which is passed to further work-up for recovering olefin oxide product and non-reacted olefin (not shown). The separated aqueous phase (8) is passed to a cross flow nanofiltration (11) by a pump (10) providing the pressure necessary for nanofiltration. The nanofiltration provides a retentate (12) enriched in manganese complex, which is recycled to the loop reactor, and a permeate (13), which is passed to recovery of dissolved olefin and olefin oxide (not shown).

LIST OF REFERENCE SIGNS

1 Circulation pump
2 Heat exchanger
3 Catalyst
4 Hydrogen peroxide
5 Olefin
6 Reaction mixture
7 Centrifuge
8 Separated aqueous phase
9 Separated organic phase
10 Pump
11 Nanofiltration
12 Retentate
13 Permeate

The invention claimed is:

1. A method for the epoxidation of an olefin, comprising:
a) continuously reacting the olefin with hydrogen peroxide in a mixed reactor in the presence of a water soluble epoxidation catalyst comprising a manganese complex, wherein the reaction is carried out in a reaction mixture comprising an aqueous liquid phase and an organic liquid phase with mixing of the liquid phases;
b) continuously withdrawing reaction mixture from the mixed reactor and separating the withdrawn reaction mixture into a separated aqueous phase and a separated organic phase; and
c) continuously recycling part of the separated aqueous phase into the mixed reactor by nanofiltration of the separated aqueous phase with a nanofiltration membrane providing a retentate enriched in manganese complex and recycling all or a part of said retentate into the mixed reactor;
wherein the combined hold-up time of aqueous phase in steps b) and c), defined as the ratio of the total volume occupied by aqueous phase in steps b) and c) to the volumetric flow rate of recycled separated aqueous phase, is less than 15 minutes.

2. The method of claim 1, wherein in step b) the withdrawn reaction mixture is separated with a centrifuge.

3. The method of claim 2, wherein the centrifuge provides an acceleration of at least 50 000 ms$^{-2}$.

4. The method of claim 2, wherein the centrifuge is a conical plate centrifuge.

5. The method of claim 1, wherein the nanofiltration is carried out with cross flow over the nanofiltration membrane.

6. The method of claim 1, wherein the nanofiltration membrane comprises a separation layer made from a polyamide.

7. The method of claim 1, wherein the mixed reactor is a loop reactor.

8. The method of claim 1, wherein no acid is added except in step a).

9. The method of claim 1, wherein the olefin is propene or allyl chloride.

10. The method of claim 1, wherein the manganese complex comprises a 1,4,7-trimethyl-1,4,7-triazacyclonane ligand.

11. The method of claim 1, wherein the reaction is carried out in the presence of an oxalate buffer.

12. The method of claim 1, wherein in step a), the pH of the aqueous liquid phase is maintained in the range from 2.5 to 5.

13. The method of claim 9, wherein the manganese complex comprises a 1,4,7-trimethyl-1,4,7-triazacyclonane ligand.

14. The method of claim 13, wherein the reaction is carried out in the presence of an oxalate buffer.

15. The method of claim 14, wherein in step a) the pH of the aqueous liquid phase is maintained in the range from 2.5 to 5.

16. The method of claim 15, wherein the nanofiltration is carried out with cross flow over the nanofiltration membrane.

* * * * *